US011243169B1

(12) United States Patent
Kadi et al.

(10) Patent No.: US 11,243,169 B1
(45) Date of Patent: Feb. 8, 2022

(54) METHOD FOR DETECTING AND MEASURING HEAVY METALS

(71) Applicant: King Abdulaziz University, Jeddah (SA)

(72) Inventors: Mohammad W. Kadi, Jeddah (SA); Reda Mohamedy Mohamed, Jeddah (SA); Adel Ali Ismail, Cairo (EG); Mohd Faisal, Najran (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/181,335

(22) Filed: Feb. 22, 2021

(51) Int. Cl.
*G01N 21/78* (2006.01)
*G01N 21/31* (2006.01)
*G01N 31/22* (2006.01)
*G01N 33/18* (2006.01)

(52) U.S. Cl.
CPC ............ *G01N 21/78* (2013.01); *G01N 21/31* (2013.01); *G01N 31/22* (2013.01); *G01N 33/1813* (2013.01)

(58) Field of Classification Search
CPC ......... G01N 21/78; G01N 21/32; G01N 31/22
See application file for complete search history.

(56) References Cited

U.S. PATENT DOCUMENTS 3,843,325 A * 10/1974 Schmitt et al. ........ G01N 31/22
436/80

OTHER PUBLICATIONS

Synthesis, characteriazation and application of poly(acrylamide-co-methylenbisacrylamide) nanocomposite as a colorimetric chemosensor for visual detection of trace levels of Hg and Pb ions. Roya Sedghi, Bahareh Heidari, Mohammad Behbahani Journal of Hazardous Materials 285, 2015, 109-116 (Year: 2015).*
Heterogeneous colorimetric sensor for mercuric salts Emilio Palomares, Ramon Vilar, James R. Durrant Chem. Commun., 2004, 362-363 (Year: 2004).*

* cited by examiner

*Primary Examiner* — Brian R Gordon
*Assistant Examiner* — Dwan A Gerido
(74) *Attorney, Agent, or Firm* — W&C IP

(57) ABSTRACT

A method of detecting one or more heavy metals in a sample solution is provided. The disclosure includes adding a dye to the sample solution having the one or more heavy metals to produce a color mixture. Mesoporous $TiO_2$ NPs are added to the color mixture to preconcentrate metal-dye complex onto the surface of the mesoporous $TiO_2$ NPs. Presence of the one or more heavy metals is detected by change in color within about 30 seconds via a naked eye. The disclosure further includes a method of determining concentration of one or more heavy metals in a sample solution by absorbance.

8 Claims, 8 Drawing Sheets

FIG. 3A
FIG. 3B
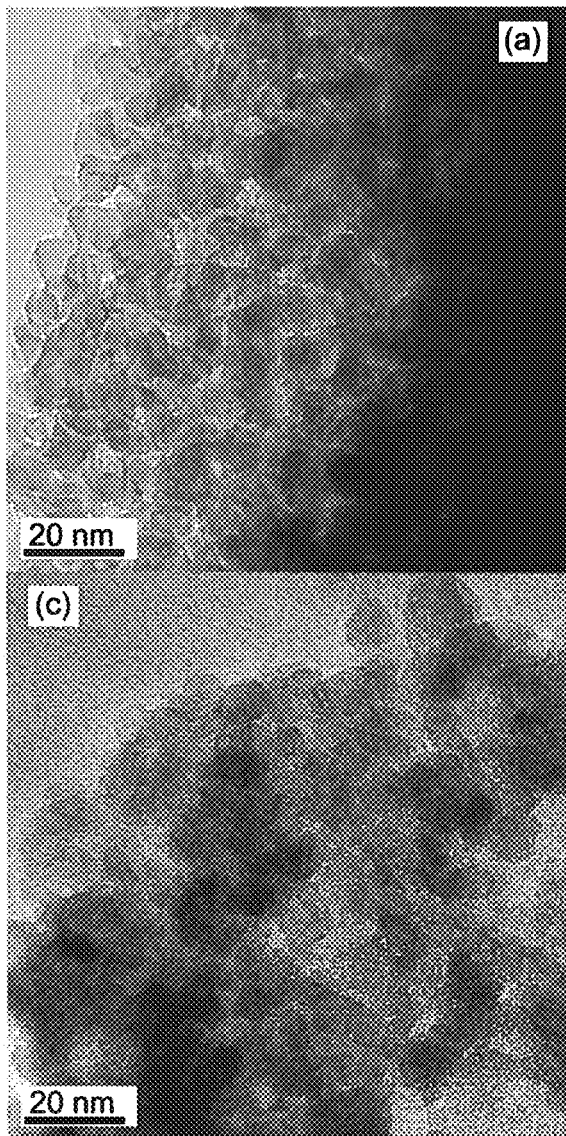
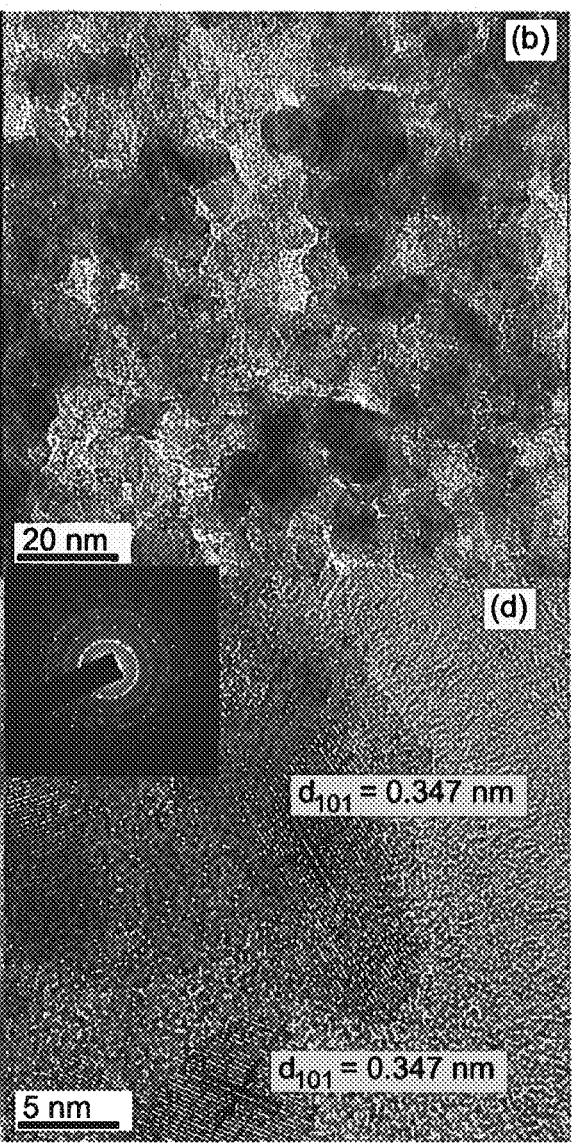
FIG. 3C
FIG. 3D

METHOD FOR DETECTING AND MEASURING HEAVY METALS

TECHNICAL FIELD

The present disclosure relates to detection and measurement of one or more heavy metals in a sample solution. More specifically, the present disclosure relates to detection and measurement of one or more heavy metals in a sample solution using the chromophore of dithizone (DZ) and mesoporous $TiO_2$ nanoparticles (NPs).

BACKGROUND

Heavy metal toxicity has emerged as a major ecological and health hazard. Significantly, heavy metals percolate into the human and animal food chains and due to bioaccumulation and nondegradable state of the heavy metals, this results in several health hazards, such as cancer. Heavy metals such as lead, cadmium, arsenic, nickel, chromium, cobalt, zinc, selenium, and their salts are highly toxic even in minor quantities.

Mercury ions (Hg(II)) are considered extremely dangerous and among the predominant toxic elements in the environment. The main sources of Hg(II) come from industrial activities, for instance, the production of caustic soda, chlorine, and electrical applications may significantly endanger human health if any effluents are released into aquatic environments in the vicinity. In drinking water, the maximum permissible restriction for Hg(II) ion has been determined to be of 6 μg/L. Accidentally ingesting even traces of Hg(II) ions can destroy the reproductive system, bones, brain functions, kidney, and, liver, causing symptoms of Hg(II) poisoning, for instance, nervous disorders system, hair, vision, and hearing loss.

Considering the severe environmental and health hazards of heavy metals, especially mercury, search for efficient materials and techniques to detect and remove heavy metals and ions has proved to be a challenging task. Although several techniques have been devised for the detection and removal of heavy metal ions, various disadvantages exist. For example, several techniques are very costly and operationally very complex. The adsorption approach is an efficient technique for eliminating toxic elements from aquatic environments. Diverse adsorbents such as coal, clay minerals, zeolite, chitosan and iron oxide have been utilized, however, the technique has limited potential applications because of low adsorption capacity, on the other hand, it doesn't allow for easy detection of Hg ions.

Moreover, the detection of heavy metal ions at ultra-trace levels is challenging due to the low sensitivity and selectivity of currently known techniques. Thus, there is a need for developing methods and systems that are fast, simple, industrially robust, sensitive, specific, and cost-effective. Further, there is a need for methods and systems having high mechanical stability, high adsorption capacity, high surface area, and recyclability for repeated detection and removal of heavy metals. Therefore, a facile selective, sensitive, and speedy heavy metal ions detection is desirable for analysis from high to ultra-trace concentrations.

BRIEF DESCRIPTION OF THE DRAWINGS

The drawings described below are for illustration purposes only and are not intended to limit the scope of the present disclosure in any way.

FIG. 3(a) shows Transmission electron microscopy (TEM) images of mesoporous $TiO_2$ NPs with DZ-$TiO_2$;

FIG. 3(b) shows TEM images of mesoporous $TiO_2$ NPs with Hg-DZ/$TiO_2$;

FIG. 3(c) shows a High Resolution Transmission Electron Microscopy (HR-TEM) image of mesoporous $TiO_2$ NPs for the lattice fringes of the anatase phase with the typical distances, i.e., $TiO_2$ (101) (3.47 Å);

FIG. 3(d) show insets depicting the Selected Area Electron Diffraction (SAED) patterns for the anatase phase of mesoporous $TiO_2$ NPs;

FIG. 4(c) shows % removal of Hg(II) ions as a function of pH (ranges 1-4) using 10 mg $TiO_2$ in 20 ml of 0.1 ppm Hg (II) ions after 2 minutes of reaction time;

SUMMARY

Figure 1A:
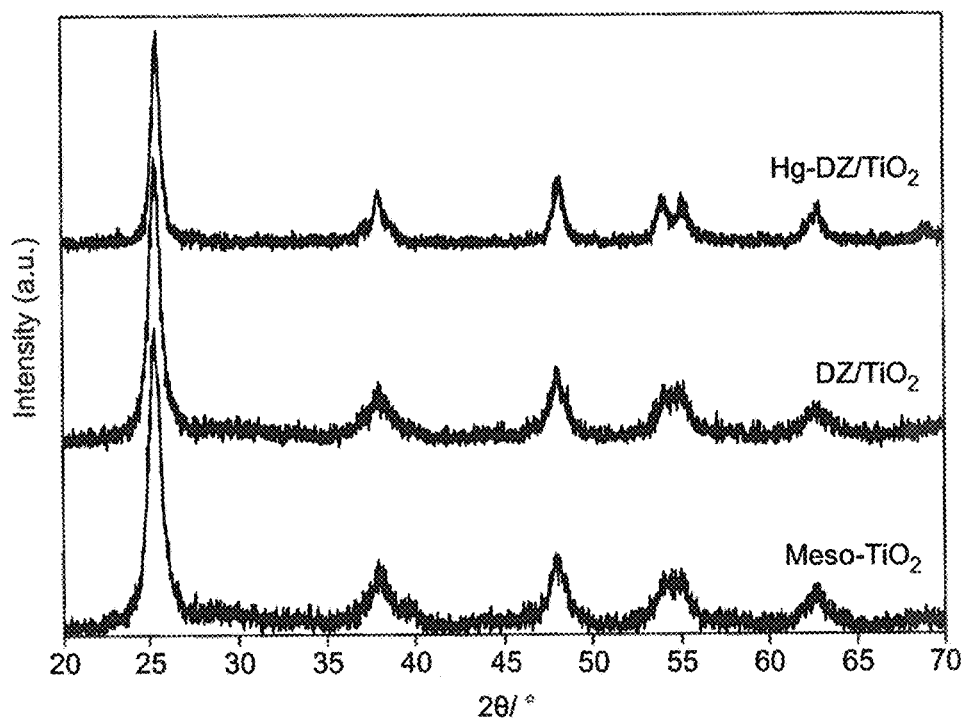
FIG. 1(a) is an XRD pattern of mesoporous $TiO_2$, DZ-$TiO_2$ and Hg-DZ/$TiO_2$.

The present disclosure relates to methods of detecting and measuring concentration of one or more heavy metal ions in a sample solution. The method includes adding a dye to the sample solution containing the heavy metal ions and then adding mesoporous $TiO_2$ NPs to preconcentrate and detect the one or more heavy metals in the sample solution.

In one aspect, the present disclosure includes a method of detecting one or more heavy metals in a sample solution. The method includes adding a dye to the sample solution having the one or more heavy metals to produce a color mixture. Mesoporous TiO$_2$ NPs are added to the color mixture to preconcentrate resulting metal-dye complex onto a surface of the mesoporous TiO$_2$ NPs. The one or more heavy metals present is detected by a change in color within about 30 seconds via a naked eye.

In another aspect, the present disclosure includes a method of determining concentration of one or more heavy metals in a sample solution. The concentration of the one or more heavy metals in the sample solution is determined by adding a dye to the sample solution to produce a color mixture. TiO$_2$ NPs are added in a solution to produce mesoporous TiO$_2$ NPs. The mesoporous TiO$_2$ NPs are added to the color mixture to preconcentrate resulting metal-dye complex onto a surface of the mesoporous TiO$_2$ NPs. The mixture containing the metal ions-dye complex onto the surface of mesoporous TiO$_2$ NPs is extracted and absorbance of the extract is measured via spectroscopy determining the concentration of the one or more heavy metals.

In some embodiments, the one or more heavy metals present in the sample solution includes mercury, lead, cadmium, arsenic, nickel, chromium, cobalt, zinc, selenium, and salts thereof. In one embodiment, the sample solution includes mercury ions thereof. In some embodiments, the dye added to the sample solution includes dithizone, coumarin, rhodamine derivatives, azo dyes, boron-dipyrromethene (BODIPY) dyes, 2-[3-(2-aminoethylsulfanyl) propylsulfanyl] ethanamine, fluorescein derivatives, cyanine dyes, or a combination thereof. In one embodiment, the dye added to the sample solution includes dithizone. In some embodiments, the solution containing the TiO$_2$ NPs is used for at least 5 cycles of determining the concentration of the one or more metals in the sample solution. In certain embodiments, the detection and measurement of the concentration of the one or more heavy metals in a sample solution occurs at nanomolar concentrations.

The foregoing as well as other features and advantages of the present disclosure will be more fully understood from the following description, examples, and claims.

DETAILED DESCRIPTION

The present disclosure as demonstrated in this application, includes mere illustrations of the invention. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention. Any method steps, and processes described herein are not to be construed as necessarily requiring their performance in the particular order discussed or illustrated, unless specifically identified as an order of performance. It is also to be understood that additional or alternative steps may be employed, unless otherwise indicated.

The present disclosure provides methods of detecting and determining the concentration of one or more heavy metals in a sample solution. The methods include adding a dye to the sample solution to produce a color mixture, preparing, and adding mesoporous TiO$_2$ NPs to the color mixture to preconcentrate metal-dye complex onto the surface of the mesoporous TiO$_2$ NPs. Presence of the one or more heavy metals is detected by change in color detected within about 30 seconds via a naked eye. Further, the mixture containing the metal-dye complex onto the surface of mesoporous TiO$_2$ NPs is extracted and absorbance of the extract is measured via spectroscopy determining the concentration of the one or more heavy metals.

As used herein, "preconcentrate" refers to any methods or processes that increase the concentration of one or more heavy metals in a sample solution prior to detection or measurement to detectable concentrations. Different preconcentration techniques of the one or more heavy metals can be used for the methods of the present disclosure such as cloud point extraction, solid phase extraction or acid preconcentration.

As used herein, "heavy metals" include all metals, metalloids or any other known forms that are toxic to human, animal life or environment even at lower concentrations. The terms "heavy metal" and "toxic metal" are used interchangeably herein.

As used herein, "sample solution" refers to any quantity of liquid which may contain one or more heavy metals.

As used herein, "amount" refers to the level or concentration of one or more heavy metals present in a sample solution.

As used herein, "measure" or "determine" refers to any qualitative or quantitative measurements or determinations by the methods of the present disclosure.

The use of the singular herein includes the plural (and vice versa) unless specifically stated otherwise.

The use of the terms "include," "includes", "including," "have," "has," or "having," "comprise," "comprises," "comprising" or the like should be generally understood as open-ended and non-limiting unless specifically stated otherwise.

It is understood that the order of steps or order for performing certain actions can be changed so long as the intended result is obtained. Moreover, two or more steps or actions may be conducted simultaneously.

As used herein, the term "about" refers to a ±20% to ±10% variation from the nominal value unless otherwise indicated. For example, in certain applications, such as heavy metal measurements in aqueous solutions, the term "about" can refer to a ±5%, or a ±2.5%, or a ±1% variation from the nominal value or a fixed variation from the nominal value, for example, ±0.1 units or ±0.2 units.

The present disclosure includes the method of detecting the one or more heavy metals in a sample solution. The method includes adding a dye to the sample solution containing the one or more heavy metals to produce a color mixture. Further, adding mesoporous TiO$_2$ NPs to the color mixture to preconcentrate metal-dye complex onto the surface of the mesoporous TiO$_2$ NPs; and detecting the presence of the one or more heavy metals based on change in color within about 30 seconds via a naked eye.

The disclosure includes using a dye or a combination of dyes selected from a group comprising dithizone, coumarin, rhodamine derivatives, azo dyes, boron-dipyrromethene (BODIPY) dyes, 2-[3-(2-aminoethylsulfanyl) propylsulfanyl] ethanamine, fluorescein derivatives, cyanine dyes. In some embodiments, the dye added to the sample solution containing the one or heavy metals is dithizone. In certain embodiments, the dye solution is prepared, and a portion of the solution is used to perform the methods of the present disclosure for multiple number of times.

The present disclosure further relates to the detection of the one or more heavy metals in the sample solution from a group comprising mercury, lead, cadmium, arsenic, nickel, chromium, cobalt, zinc, selenium, and salts thereof. In some embodiments, the method of detection comprises detecting mercury ions or salts or a combination thereof in a sample solution.

The disclosure also includes the detection of the one or more heavy metals in a sample solution at nanomolar concentrations. In some embodiments, the detection of the one or more heavy metals in the sample solution occurs at a nanomolecular concentration of about $2.0 \times 10^{-9}$ to $5.0 \times 10^{-9}$ molL$^{-1}$. In an embodiment, the detection of the one or more heavy metals in the sample solution occurs at a nanomolecular concentration of about $2.3 \times 10^{-9}$ molL$^{-1}$.

Since the heavy metals can be present in trace to ultra-trace concentrations, the detection and precise quantification becomes difficult. Therefore, the present disclosure includes preconcentrating the one or more heavy metals in the sample solution before detection. The methods include preconcentrating the one or more heavy metals onto the surface of mesoporous TiO$_2$ NPs for the ease of detection and determination of the concentration in the sample solution.

In various embodiments of the present disclosure, the sample solution is selected from a group comprising drinking water, industrial effluents, bodily fluid, or a beverage suitable for human consumption. In some embodiments, the beverage includes carbonated drink, juice, soup, or an alcoholic beverage. In yet other embodiments, the bodily fluid includes blood, urine, saliva, plasma, or lymph.

In some embodiments, the method of detection includes detecting presence of Hg(II) ions in water. In one embodiment, the sample solution is drinking water. In another embodiment, the method further includes removing the Hg(II) ions and determining the concentration of the Hg(II) ions present in the drinking water. In some embodiments, the sample solution includes soil or food or pharmaceuticals for detecting and determining the presence of one or more heavy metals.

The mesoporous TiO$_2$ NPs of the present disclosure show high degree of regeneration. Thus, in various embodiments, the mesoporous TiO$_2$ NPs are used for at least 5 cycles of detection. In some embodiments, the mesoporous TiO$_2$ NPs are recovered for further sensing and detection through photodegradation process by using UV illumination. In some embodiments, the mesoporous TiO$_2$ NPs are used for at least 500 cycles of detection with no effect on the rate of detection of the one or more heavy metals.

The method of detection is specific and selective based on the pH of the mixture solution even in the presence of foreign interferences. Thus, in some embodiments, the sensing method detects the one or more heavy metal in presence of any interfering cations, such as Co(II), Ag(I), Ni(II), Pb(II), Ca(II), Zn(II), Mn(II), Cd(II), Fe(III)), and Cu(II), and anions such as $CH_3COO^-$, $CO_3^{-2}$, $NO_3^-$ and $SO_4^{-2}$ even at 1000 times greater than Hg(II) ions concentration.

The present disclosure also includes the method of determining concentration of the one or more metals in a sample solution. The method includes adding a dye to the sample solution containing the one or more heavy metals to produce a color mixture and adding the mesoporous TiO$_2$ NPs to the color mixture to preconcentrate metal-dye complex onto the surface of the mesoporous TiO$_2$ nanoparticles. The method includes extracting the mixture containing the metal dye complex onto the surface of mesoporous TiO$_2$ NPs and measuring an absorbance of the extract via spectroscopy. The concentration of the one or more metals is determined based on the absorbance. In one embodiment, the absorbance of the extract is measured by inductively coupled plasma atomic emission spectroscopy, atomic absorption spectrometry (AAS), atomic emission/fluorescence spectrometry (AES/AFS), inductively coupled plasma optical emission spectrometry (ICP-OES), or a combination thereof. In some specific embodiments, the absorbance of the extract is measured by inductively coupled plasma atomic emission spectroscopy. In various embodiments, the mesoporous TiO$_2$ NPs are used for at least 5 cycles of detection. Further, the one or more heavy metals in the sample solution are detected from a group comprising mercury, lead, cadmium, arsenic, nickel, chromium, cobalt, zinc, selenium, and salts thereof. In some embodiments, the method of detection comprises detecting mercury ions or salts or a combination thereof in a sample solution.

The present disclosure also provides preconcentrating the one or more heavy metals in the sample solution before removal. In one embodiment, the disclosed method includes adding the mesoporous TiO$_2$ NPs to the color mixture to preconcentrate metal-dye complex onto a surface of the mesoporous TiO$_2$ NPs. The metal-dye complex formation results in the change in the color of the solution indicating the presence of the one or more heavy metals present in the solution. To determine the concentration of the one or more heavy metal detected in the solution, the metal-dye complex onto the surface of the mesoporous TiO$_2$ NPs is extracted. In some embodiments, the metal-dye complex onto the surface of mesoporous TiO$_2$ NPs is filtered by using a filter paper. In one embodiment, the filtration is carried out by using a cellulose acetate filter paper. In yet another embodiment, the metal-dye complex onto the surface of mesoporous TiO$_2$ NPs is extracted from the solution by solid phase extraction (SPE). In other embodiments, methods such as adsorption, membrane filtration, back extraction or a combination of these methods. The absorbance of the resulting extract is measured by inductively coupled plasma atomic emission spectroscopy to determine the concentration of the one or more heavy metals present in the solution. In another embodiment, the concentration of the one or more heavy metals present in the sample solution is determined by flame atomic absorption spectroscopy (F-AAS). Thus, depending upon the sample solution the concentration of the metal-dye complex onto the surface of the mesoporous TiO$_2$ nanoparticles can be determined by chromatography techniques, atomic absorption spectrometry (AAS), atomic emission/fluorescence spectrometry (AES/AFS), inductively coupled plasma optical emission spectrometry (ICP-OES); neutron activation analysis (NAA), X-ray fluorescence (XRF), anodic striping voltammetry (AVS), or a combination of several techniques known to determine the heavy metal concentrations.

Further, the disclosed method includes determining the one or more heavy metals in a sample solution at nanomolar concentrations. In some embodiments, the one or more heavy metals in the sample solution are at a nanomolecular concentration of about $2.0 \times 10^{-9}$ to $5.0 \times 10^{-9}$ molL$^{-1}$. In an embodiment, the one or more heavy metals are at a nanomolecular concentration of about $2.3 \times 10^{-9}$ molL$^{-1}$ The sample solution is selected from a group comprising drinking water, industrial effluents, bodily fluid, or a beverage suitable for human consumption. In some embodiments, the beverage includes carbonated drink, juice, soup, or an alcoholic beverage. In specific embodiments, the bodily fluid includes blood, urine, saliva, plasma, or lymph. In some embodiments, the sample solution includes soil or food or pharmaceuticals for detecting and determining the presence of one or more heavy metals.

In an embodiment, the method of determining the concentration of the one or more heavy metals includes removal of Hg(II) ions from water. In one embodiment, the sample solution is drinking water. In another embodiment, the method further includes removing the mercury ions and determining the concentration of the mercury ions present in the drinking water.

The present disclosure further includes the detection of color change specific to one or more heavy metals. Depending on the one or more heavy metal to be detected and measured, the pH of the solution can be adjusted accordingly. Thus, in an embodiment, for Hg(II) ions, the color of the solution changes from beige to reddish brown indicating high concentration of Hg(II) ions in the solution. In another embodiment, the color the solution containing Hg(II) changes to light brown or yellow indicating lower concentrations of Hg(II) ions. In one example, the color changes from beige to red indicating higher concentration of Hg(II) present in the solution. In one embodiment the method detects the presence of Cu ions in the solution by the change in the color of the solution to brown. Thus, according to the methods of the present disclosure, different color variations specific to each heavy metal and at a certain pH determines the detection and concentration of the one or more heavy metals present in the sample solution.

In one of the embodiments of the present disclosure, appropriate personnel can employ the method of detection to quickly detect the presence of heavy metals in a sample on field visits or during inspection. Thus, a sample of water may be tested quickly and conveniently at location to ensure the quality of water.

According to certain embodiments, the intensity of the color of the sample solution using the method of present disclosure depends on the concentration of the one or more heavy metals present in the solution. Thus, a brighter and intense color formation indicates a higher concentration of heavy metals in the sample solution. In certain embodiments, the methods of present disclosure may be implemented in many specific formats known to those skilled in the art, including through use of various high throughput clinical laboratory analyzers or in field or home testing devices.

While most of the methods proposed in the prior art require utilizing complex operation and are lengthy and time consuming, the methods of the present disclosure are advantageous in providing the results within 30 seconds in a single step.

Experimental Results

Mesoporous $TiO_2$ NPs were synthesized employing a sol-gel approach in the existence of the F127. In a typical method, 1.6 g of F127 was dissolved in 30 mL of $C_2H_5OH$ through stirring, then, 0.74 mL and 2.3 mL of HCl and $CH_3COOH$, respectively, were added with continued stirring for 60 min and subsequently, 3.5 ml of TBOT was added to the mixture [A. A. Ismail, D. W. Bahnemann, L. Robben, V. Yarovyi, M. Wark. Chem. Mater. 2010; (22:108-116)]. The mixture was dried at a relative humidity of 40-80% and 40° C. for 12 h continued drying at 65° C. overnight. The obtained sample was calcinated in the air at 450° C. for 4 h at a heating rate and a cooling rate of 1° C./min and 2° C./min, respectively to eliminate F127 surfactant and to produce mesoporous $TiO_2$ NPs.

X-ray diffraction (XRD) patterns were employed, for example, on a PANalytical X' port diffractometer using Cu K$\alpha$1/2, $\lambda\alpha$1=154.060 pm, $\lambda\alpha$2=154.439 pm radiation. JEOL JEM-2100E-UHR field-emission instrument was used for measuring Transmission electron microscopy (TEM) images equipped with a Gatan GIF 2001 energy filter and a 1 k-CCD camera to get electron energy loss spectroscopy (EEL) spectra at 200 kV. Quantachrome Autosorb 3B was used for determining the $N_2$ adsorption-desorption isotherms at 77 K using after vacuum-drying at 200° C. for 12 hours. The sorption data were measured to utilize the Barrett-Joyner-Halenda (BJH) model with Halsey equation. Perkin Elmer Raman Station 400 was used to record Raman spectroscopy. Fourier-transform infrared spectroscopy (FT-IR) spectra were determined with a BRUKER FRA 106 spectrometer. Reflectance spectrum was determined applying UV-Visible spectrophotometer (lambda 950 Perkin Elmer) at room temperature. The Hg (II) ions detection were carried out at diverse ranges of Hg (II) ion concentrations ranging from $4.98\times10^{-9}$ molL$^{-1}$ to $4.985\times10^{-6}$ molL$^{-1}$. 5 mg DZ was added to 100 mL of ethanol to be ready for colorimetric detection. The pH values 1 and 2 were adjusted by adding a buffer 0.2M KCl—HCl solution. The pH value at 2.9 was adjusted by adding 0.1 M $C_8H_5KO$—HCl. Also, 0.1M $CH_3COOH$—$CH_3COONa$ was employed to adjust pH at 4. Experiments were performed utilizing varied Hg (II) ion concentrations at the range of $4.98\times10^{-9}$ molL$^{-1}$ to $4.985\times10^{-6}$ molL$^{-1}$.

For the Hg (II) ions detection, 20 mL of Hg (II) ion solution at a desired pH and 1.5 mL DZ (5% w/v) were mixed, then 10 mg of mesoporous $TiO_2$ NPs was added through stirring for 2 min to get the equilibrium adsorption. The color of the suspension solution was completely turned from beige to reddish brown upon addition of Hg (II). The collected powder (Hg(II)-DZ)/$TiO_2$ was separated employing cellulose acetate (25 mm) filter paper. The absorbance of obtained powder color was measured applying UV-Visible spectrophotometer (lambda 950 Perkin Elmer). Inductively coupled plasma atomic emission spectroscopy (ICP-AES) was used to determine Hg (II) ions concentration in the filtrate to determine the removal efficiency. The experiments were duplicated to confirm the reproducibility and consistency of the findings. To evaluate the regeneration, the mesoporous $TiO_2$ NPs, Hg(II) ions was eluted by 0.001M $HNO_3$ study followed by UV illumination for self-cleaning $TiO_2$ surface by degrading of DZ. After the regeneration procedure, the mesoporous $TiO_2$ NPs was recycled for five times to investigate its durability and reusability. The limit of detection (LOD) of Hg(II) ions was determined applying the calibration curve of the linear part of the absorbance of [Hg-DZ]/$TiO_2$ against Hg(II) ions concentration as follows [S. A. El-Safty, A. A. Ismail, H. Matsunaga, F. Mizukami. *Adv. Funct. Mater.* 2008; (18: 1485-15000)]

$$LOD = K\,Sb/m \quad (1)$$

where Sb is the standard deviation for the blank, K is the confidence factor=3, and m the calibration curve slope. The relative Sb for the measured absorbance at $\lambda$ max=495 nm was determined to be 0.005% after 5 consecutive experiments, suggesting a good reproducibility of the constructed optical sensor.

Figure 1B:
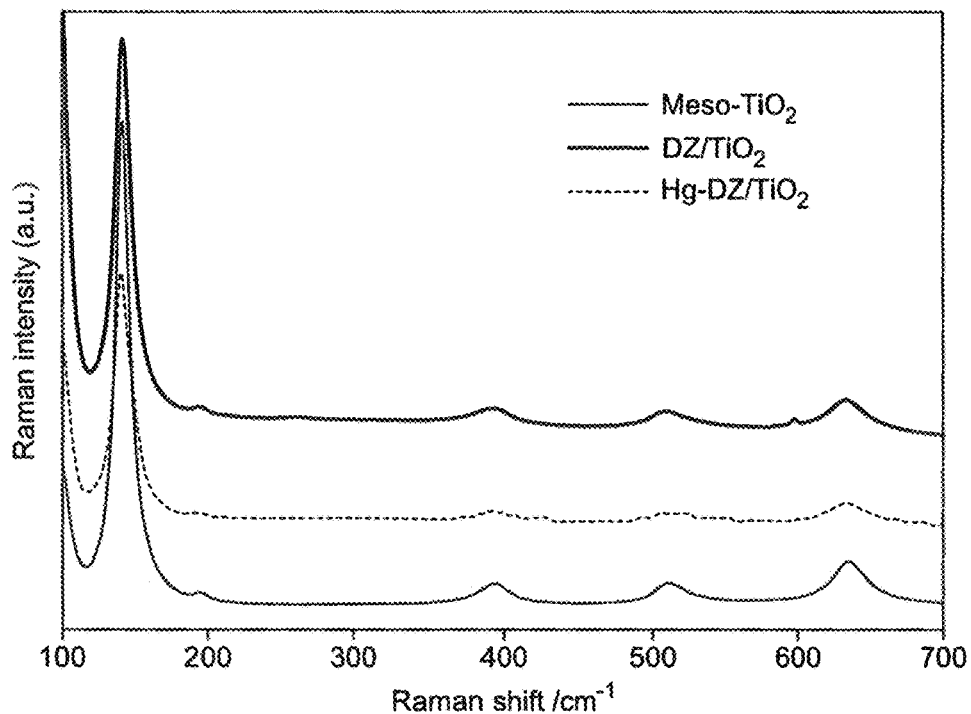
FIG. 1(b) is a Raman spectrum of mesoporous $TiO_2$, DZ-$TiO_2$ and Hg-DZ/$TiO_2$.

Referring to FIG. 1(a) X-ray powder diffraction (XRD) patterns of the pristine $TiO_2$ nanoparticles DZ-$TiO_2$ (Dithizone-$TiO_2$) and [Hg-DZ]/$TiO_2$ samples are shown and illustrated according to various embodiments of the present disclosure. The findings show that $TiO_2$ characteristics include the anatase phase with lattice planes at (101), (004), (200), (211) and (213) to indicate that mesoporous $TiO_2$ was formed in anatase phase. The intensity of the mean peak of anatase phase did not change upon addition of DZ and after collecting [DZ-Hg] complex onto the mesoporous $TiO_2$ surface (FIG. 1(a)). FIG. 1(b) reflects the Raman bands for the pristine $TiO_2$ NPs, DZ-$TiO_2$ and [Hg-DZ]/$TiO_2$, indicating the presence of anatase phase for six modes at 142.6 cm$^{-1}$ (Eg), 197.0 cm$^{-1}$ (Eg), 395.5 cm$^{-1}$ (B1g), 515.1 cm$^{-1}$ (A1g+B1g), and 640.0 cm$^{-1}$ (Eg) [A. A. Ismail, D. W. Bahnemann, L. Robben, V. Yarovyi, M. Wark. *Chem. Mater.* 2010; (22:108-116)].

Figure 1C:
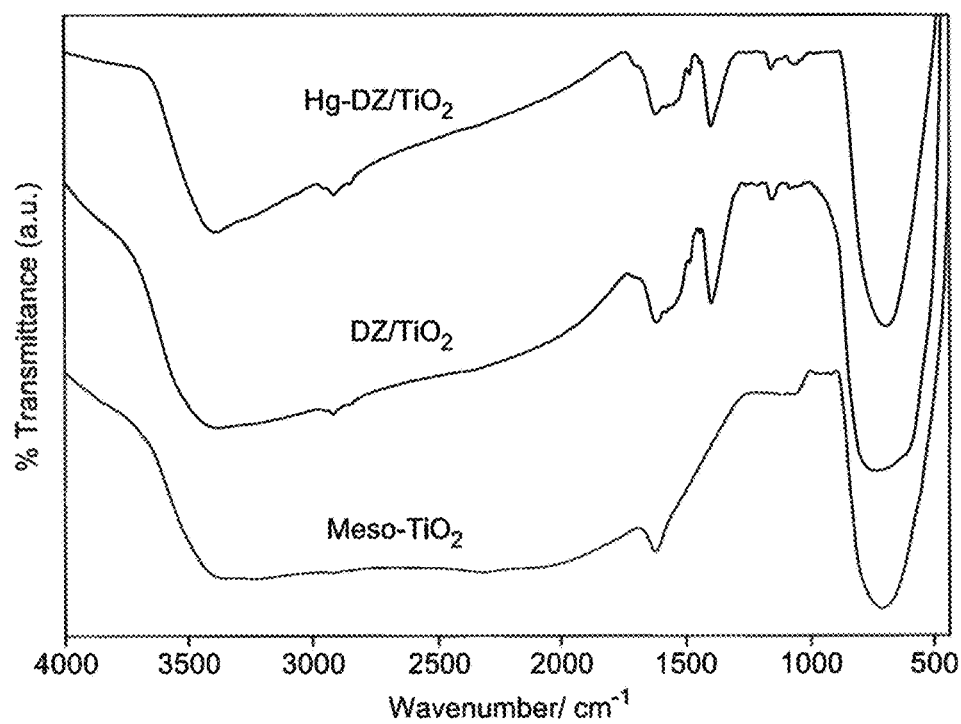
FIG. 1(c) is a Fourier-transform infrared spectroscopy (FTIR) spectrum for mesoporous $TiO_2$, DZ-$TiO_2$ and Hg-DZ/$TiO_2$.
Figure 1D:
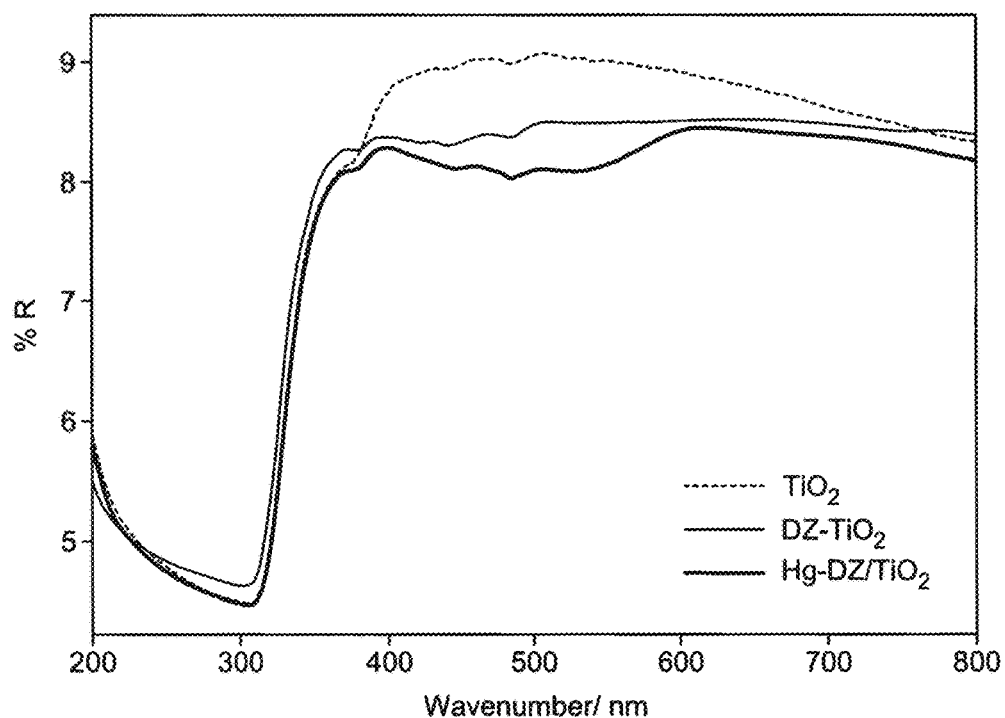
FIG. 1(d) is a diffuse reflectance spectrum for the mesoporous $TiO_2$, DZ-$TiO_2$ and Hg-DZ/$TiO_2$

The crystallinity of anatase phase shows no effect upon addition of DZ and after collecting [DZ-Hg] complex onto the mesoporous TiO$_2$ surface. Referring to FIG. 1(c) the Fourier transform infrared spectroscopy (FT-IR) spectrum for pristine TiO$_2$ NPs, DZ-TiO$_2$ and [Hg-DZ]/TiO$_2$ is displayed. The findings indicate a broad absorbance peak located at 3440 cm$^{-1}$ as a result of vibration mode of OH— and a small peak appeared ~1620 cm$^{-1}$ corresponding to the H$_2$O adsorbed vibrations and Ti—OH bonds [H. X. Li, J. X. Li, Y. N. Huo. *J. Phys. Chem. B.* 2006; (110:1559-1565)]. Interestingly, after DZ accommodating pristine TiO$_2$ NPs, FT-IR spectrum exhibited distinguished absorption peak assigned at 1415 cm$^{-1}$ matching to the C=S stretching mode, while at [Hg-DZ]/TiO$_2$ sample, this peak moved to 1380 cm$^{-1}$ due to the incorporation of Hg (II) ions to obtain C=S—Hg complex [J. Zhou, G. Zhao, J. Yang, G. Han. *Journal of Alloys and Compounds.* 2011; (509:6731-6735)]. The absorption peak for three samples, representing below 800 cm$^{-1}$ is due to the presence of TiO$_2$ lattice vibration [M. Ouzzine, M. A. Lillo-Rodenas. *Appl. Catal.* 2013; B:134-135:333-343]. Diffuse reflectance UV-visible spectra of pristine TiO$_2$ NPs, DZ-TiO$_2$ and [Hg-DZ]/TiO$_2$ are depicted in FIG. 1(d). The absorption edge of the synthesized samples was found at 355 nm; however, it is observed that there was a broad peak in a wide range at 400-650 nm as a result of visible light absorption by DZ and Hg-DZ. This confirms that the mesoporous TiO$_2$ NPs is available for regeneration several times during UV illumination.

Figure 2:
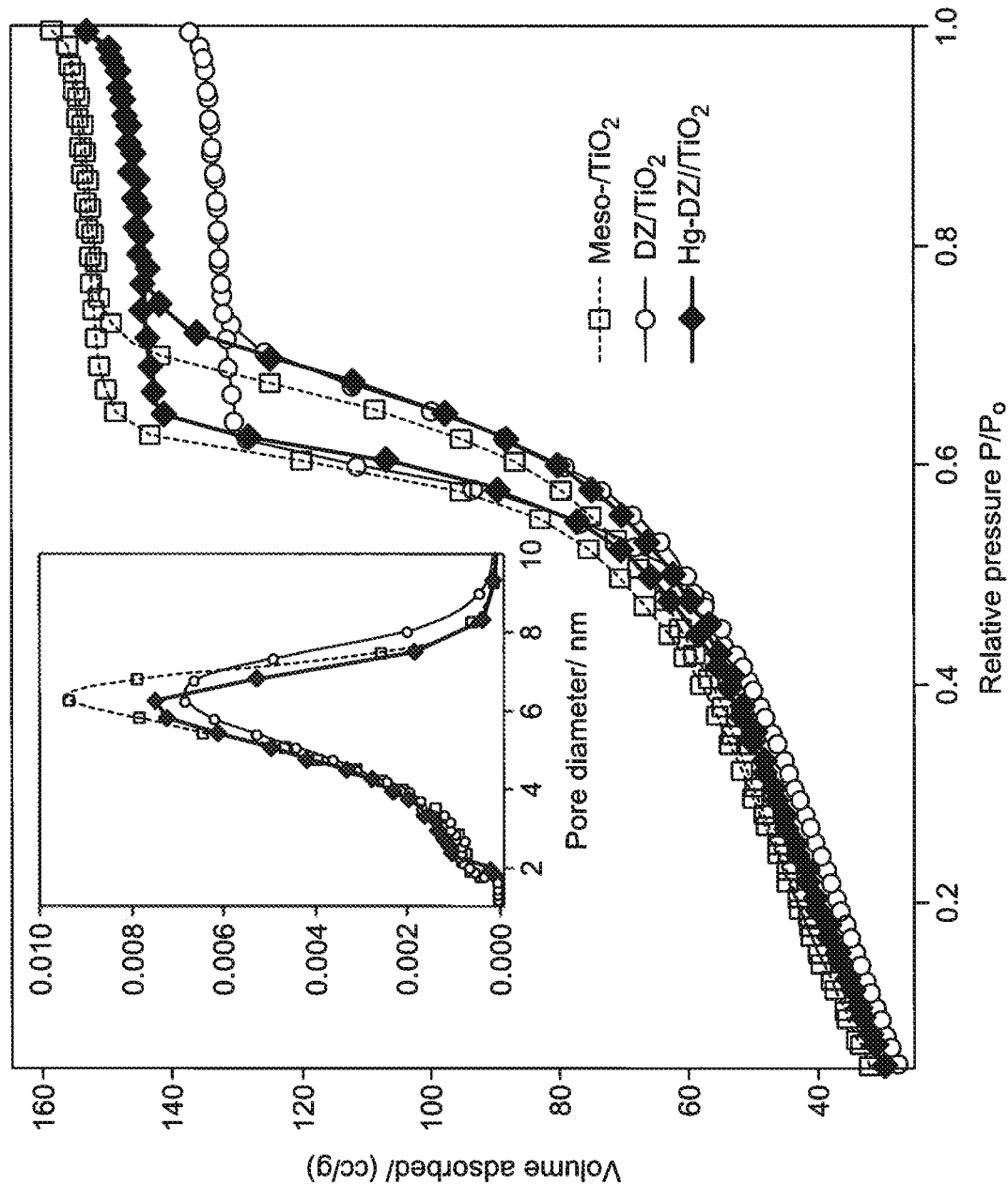
FIG. 2 shows $N_2$ sorption isotherms and pore size distributions (inset) of the mesoporous $TiO_2$, DZ-$TiO_2$ and Hg-DZ/$TiO_2$.

Referring to FIG. 2, the N$_2$ adsorption-desorption isotherms with pore size distributions of the pristine TiO$_2$ NPs, DZ-TiO$_2$ and [Hg-DZ]/TiO$_2$ samples are demonstrated. The N$_2$ isotherms revealed intense adsorption/desorption inflection, obtaining at relative pressures p/p$_o$ around 0.45-0.70. The N$_2$ isotherms revealed IV type with hysteresis loops of H$_2$ shaped show the synthesized TiO$_2$ NPs are a mesoporous structure material [A. A. Ismail, D. W. Bahnemann, L. Robben, V. Yarovyi, M. Wark. *Chem. Mater.* 2010; (22:108-116)]. After DZ and DZ-Hg complex immobilization onto the mesoporous TiO$_2$ NPs, the DZ-TiO$_2$ materials were maintained the active functional group for preconcentration, removal and detection of Hg(II) ions. TiO$_2$ NPs revealed significant pore volumes and surface area of 0.29 cm$^3$ g$^{-1}$ and 174 m$^2$ g$^{-1}$, respectively; and further were reduced to 0.22 cm$^3$ g-1 and 134 m$^2$ g$^{-1}$, respectively, indicating the DZ ligand and DZ-Hg complex anchoring the TiO$_2$ pores. In addition, the pore diameter of mesoporous TiO$_2$ NPs is minimized from 8.11 to 6.3 and 6.1 nm; this is additionally confirming the DZ ligand and DZ-Hg complex anchoring the pristine TiO$_2$ pores. Referring to FIG. 3a, Transmission electron microscopy (TEM) image of the pristine TiO$_2$ NPs exhibited that the synthesized TiO$_2$ NPs were not agglomerated, and completely uniform in shape and size with particle size ~10 nm and mesostructured in nature.

Referring to FIG. 3(b), and FIG. 3(c) reveal that the DZ ligand and Hg-DZ complex impregnated into the TiO$_2$ pores. FIG. 3(d) exhibit the High-resolution transmission electron microscopy (HR-TEM) image the lattice fringes for the anatase phase with the typical distances, i.e., TiO$_2$ (101) (3.47 Å). The selected area electron diffraction (SAED) further show that anatase nanocrystals construction.

Removal and Visualized Detection of Hg (II)

Referring to FIG. 4, mesoporous TiO$_2$ NPs are a highly active and superior candidate for the construction of sensing system owing to its large pore volume, high surface area, easy regeneration and exhibiting high optical transparency in the visible spectrum in the wide range. Mesoporous TiO$_2$ NPs were dispersed in water to obtain anionic TiO$_2$ surface and also provided more coverage of OH$^-$ generated from H$_2$O [A. A. Ismail and D. W. Bahnemann *J. Mater. Chem.* 2011; (21:11686-11707)]. Thus, to fabricate the sensing system for the Hg (II) ion recognition, mesoporous TiO$_2$ NPs possessing large pore sizes, small particle size and high surface area were taken into consideration. This distinguishing of constructed sensor enhanced the binding probability of Hg (II) ions along with associated high removal efficiency.

Hg (II) removal efficiency (% RE) was determined from the following formula: % RE=(C$_o$-C$_f$/Co)×100, where C$_o$ and C$_f$ represent the Hg (II) ions concentration in original and in the filtrate, respectively. Hg (II) ions detection was conducted for the suggested visualized sensing system to explore the removal efficiency and performance of Hg(II) ions detection in term of DZ concentration, pH values, contact time, and amount of pristine TiO$_2$ NPs demonstrated in FIG. 4).

Figure 4A:
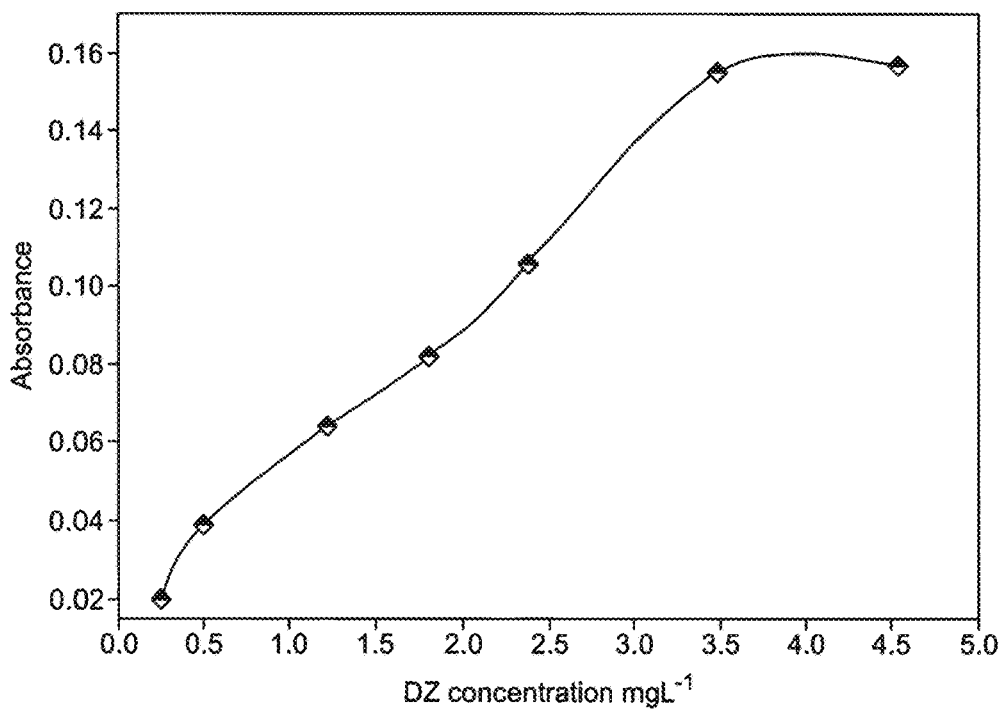
FIG. 4(a) shows effect of DZ concentration on the absorbance measured at $\lambda$=495 nm of the formed [Hg-DZ] complex between DZ and 0.1 ppm Hg (II) ions.
Figure 4B:
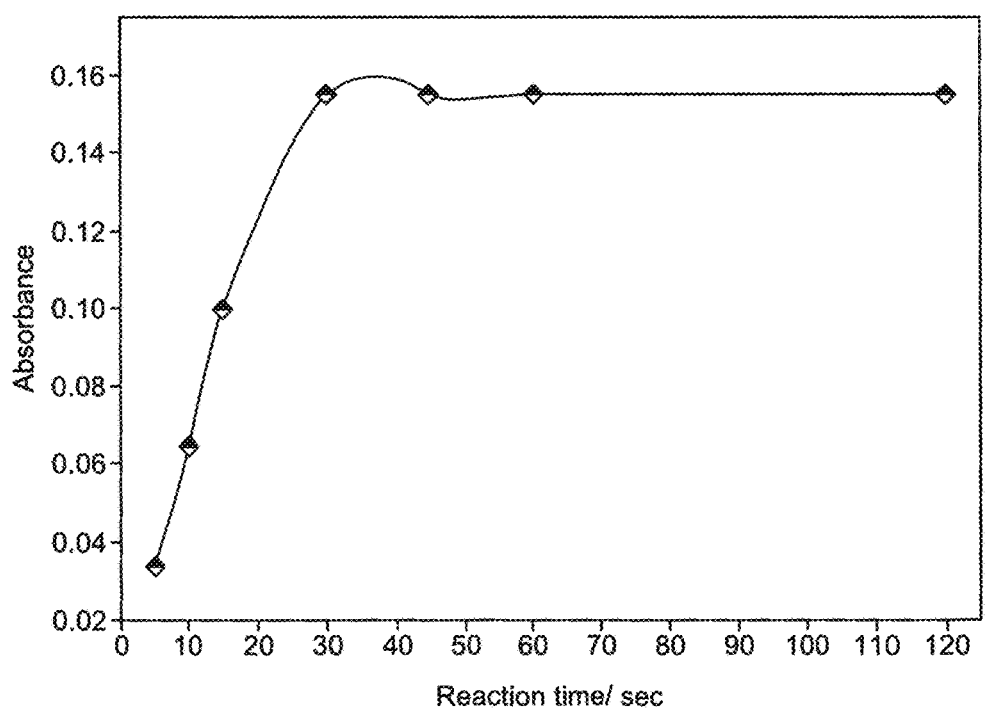
FIG. 4(b) shows concentration-dependent changes in color developed sequence of $TiO_2$-DZ after detection of Hg(II) analyte ions at different reaction times.
Figure 4C:
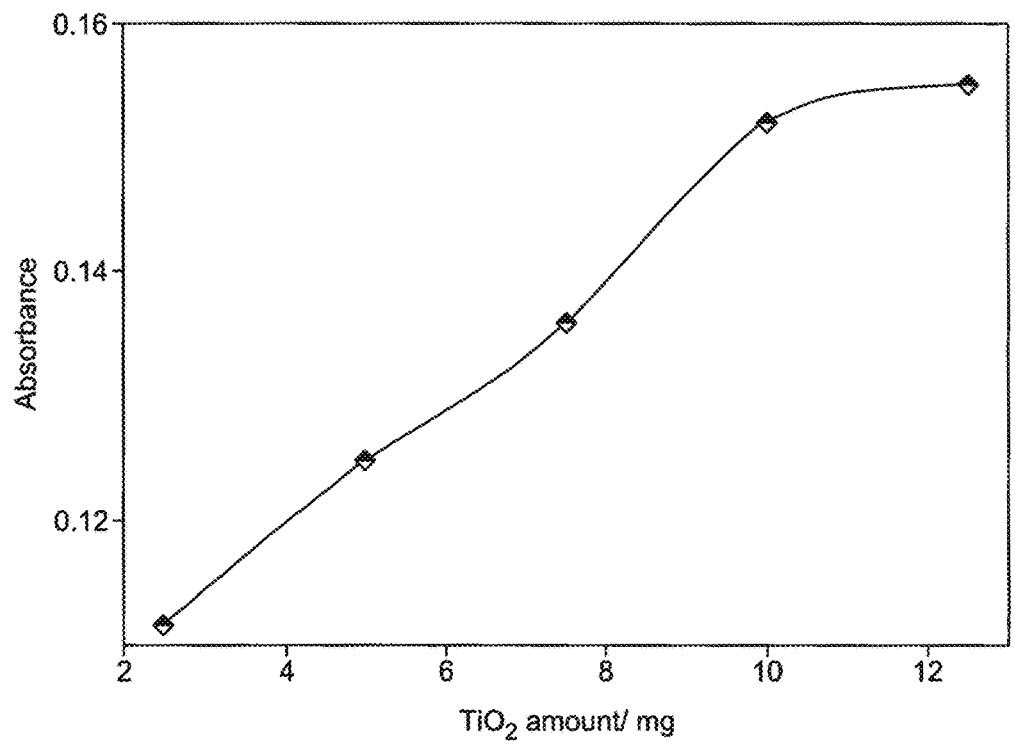
FIG. 4(c) shows % removal of Hg (II) ions at different amounts of mesoporous $TiO_2$, i.e., 2.5, 5.0, 7.5, 10.0 and 12.5 mg in 20 ml of 0.1 ppm Hg(II) ion solution after 2 minutes.
Figure 4D:
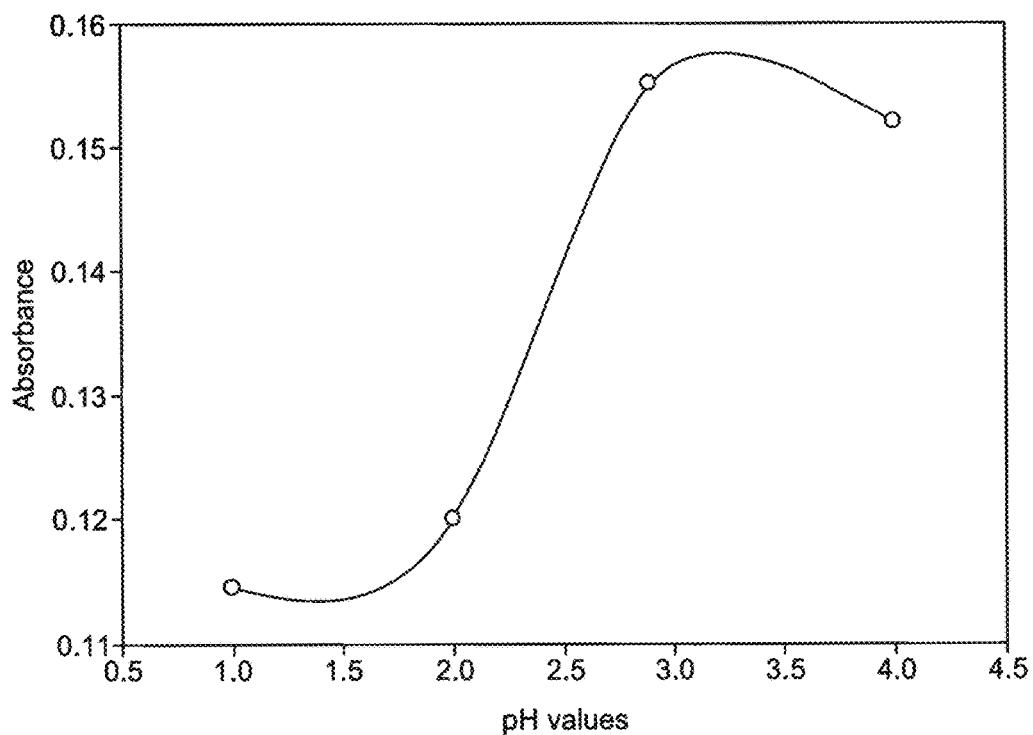

Referring to FIG. 4(a), the DZ concentration is one of the most substantial factors to detect the Hg (II) ion as it mainly determines the absorbance of the constructed complex. The effect of DZ concentration (0.249-4.55 mg/L) for the visualized detection Hg(II) ions of 4.98×10$^{-7}$ molL$^{-1}$ (0.1 ppm) was performed. The absorbance of constructed [Hg-DZ] complex over mesoporous TiO$_2$ NPs at 495 nm boosts with the increase of DZ concentration up to 3.49 mg/L. With the increase in DZ concentration above 3.49 mg/L led to levelling off absorbance. The reaction proceeds very fast in response to the introduction of DZ, consumption of Hg(II) occurs to fabricate Hg(II)-DZ complex at 3.49 mg/L of DZ. Therefore, the 3.49 mg/L of DZ concentration was chosen to continue studies.

The reaction time required to complete the interaction of DZ and Hg (II) ions to form Hg(II)-DZ complex is another important parameter. The effect of reaction time was also conducted for 120 sec and it was observed that the reaction proceeds very fast and was completed within 30 sec of reaction time as demonstrated in FIG. 4(b). No significant removal efficiency was observed after 30 sec. The amount of mesoporous TiO$_2$ NPs-based visualized sensor mainly 2.5, 5, 7.5, 10 and 12.5 mg has been carried out in 20 ml of 4.98×10$^{-7}$ molL$^{-1}$ Hg (II) ions within 30 s at pH 2.9 as demonstrated in FIG. 4(c). This also shows that constructed sensor with 2.5 mg TiO$_2$ NPs can efficiently remove 72.3% Hg (II) ions indicating the capability of the sensor construction. As the amount of highly effective TiO$_2$ NPs reproduces, the removal efficiency boosts to reach ~100% of Hg (II) ions when 10 mg of TiO$_2$ NPs was employed. The construction of Hg(II)-DZ complex over mesoporous TiO$_2$ at diverse pH values were conducted in the range of 1-4 by examining the signal intensity at their λ max shown in FIG. 4(d). The findings show the complex was completed with the increasing pH value from 1 to 2.9, then the absorbance was decreased at pH value=4. [C. Yin, J. Iqbal, H. Hu, B. Liu, L. Zhang, B. Zhu, Y. Du. *J. Hazard. Mater.* 2012; (233-234: 207-212)]. Therefore, the typical pH values to complete removal Hg(II) ions was determined at 2.9 at maximum color intensity.

Figure 5A:
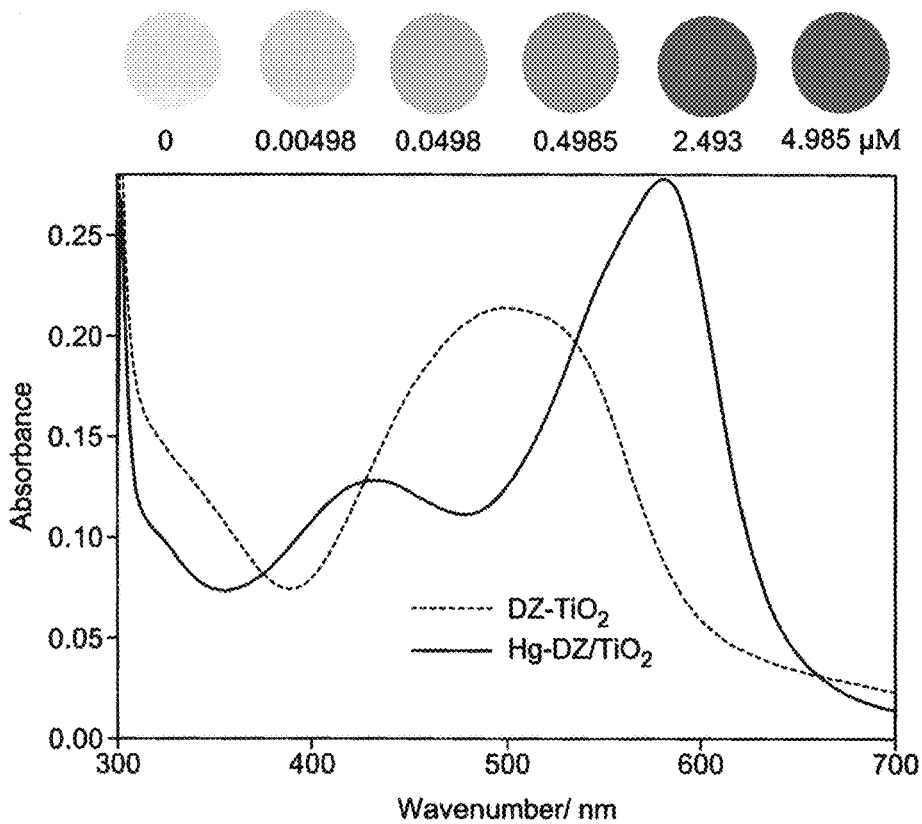
FIG. 5(a) shows change in absorption measured at $\lambda$=495 nm of newly formed [Hg-DZ] complex as a function of concentration of DZ after 30 sec of reaction time between DZ and 0.1 ppm Hg (II) ions at pH 2.9; Inset shows change in the color of the [Hg-DZ] complex with different Hg(II) concentrations in solutions.

Referring to FIG. 5(a) the spectral patterns DZ-TiO$_2$ as a blank and [Hg-DZ]/TiO$_2$ sample are exhibited. The DZ-TiO$_2$ sample reveals the maximum absorbance at 440 nm and 595 nm. The shorter and longer wavelengths matched to the thiol and the thione groups of DZ [M. Faisal, A. A. Ismail, F. A. Harraz, H. Bouzid, S. A. Al-Sayari, A. Al-Hajry.

Chem. Eng. J. 2014; (124:509-516)]. In presence of Hg (II) ions, the construction of Hg(II)-DZ complex occurs between DZ and Hg(II) ions and results in an increase in absorbance at 495 nm that corresponded to the Hg(II)-DZ complex over $TiO_2$ NPs while the absorbance at 595 nm related to thione group of DZ gradually disappeared with increase in Hg (II) ions concentration at $4.98 \times 10^{-7}$ molL$^{-1}$, the amount of formed Hg(II)-DZ complex also increases which results in a decrease in DZ concentration [C. Yin, J. Iqbal, H. Hu, B. Liu, L. Zhang, B. Zhu, Y. Du, J. Hazard. Mater. 2012; (233-234:207-212)].

Referring to FIG. 5(a) inset. the color pattern reflects by the designed sensor for blank and in the presence of Hg (II) ions over mesoporous $TiO_2$ are displayed. The beige color was obtained in the absence of Hg (II) but the fabricated sensor showed light salmon color even at very low concentration $4.98 \times 10^{-9}$ molL$^{-1}$ (0.001 ppm). With the increase in the Hg (II) ions concentration, the intensity of [Hg-DZ] complex over $TiO_2$ NPs color also increases and the color of designed sensor displayed reddish-brown color at a high concentration about $4.98 \times 10^{-6}$ molL$^{-1}$ (1 ppm). This is due to high surface area and large pore volume of mesoporous $TiO_2$ networks, which accelerated the diffusion of [Hg-DZ] complex easily with high accessibility.

Figure 5B:
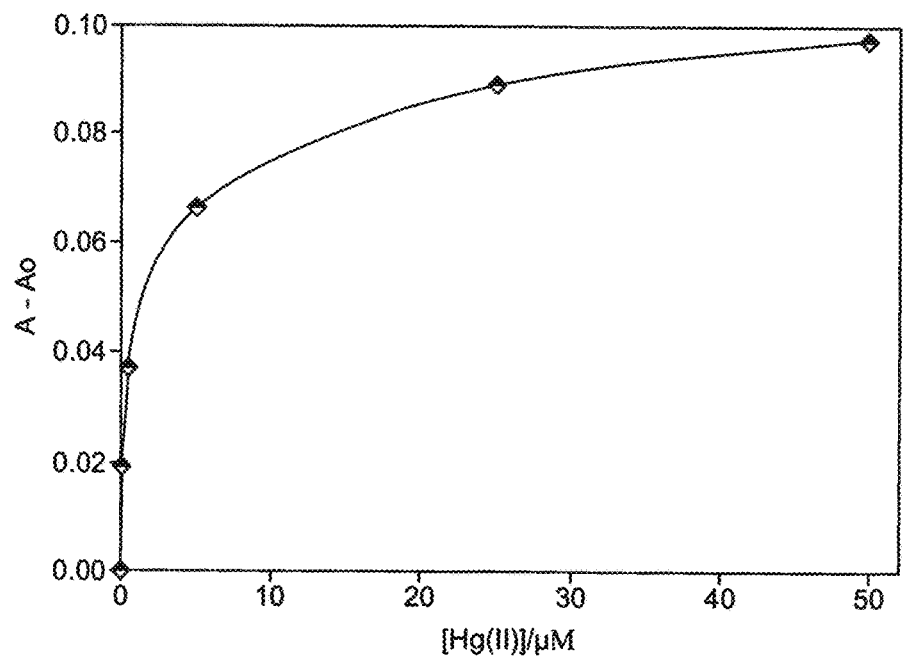
FIG. 5(b) shows a linear relationship of Hg(II) concentration at 0.00498-0.498 μM with the correlation coefficient ~$R^2$=0.99 to determine the limit of detection (LOD) which derived from the signal [Hg-DZ] complex intensity at 495 nm as a function of concentrations of Hg(II) ions.

The LOD and the linear response of the calibration curve was determined at low concentration of Hg(II) ions derived from the signal [Hg-DZ] complex intensity at 495 nm as a function of concentrations of Hg(II) ions as demonstrated in FIG. 5(b). This is also observed that a linear relationship of Hg(II) concentration at 0.00498-0.498 µM with the correlation coefficient ~$R^2$=0.99, demonstrating that the Hg(II) ions concentrations can be visually monitored with high sensitivity. Generally, up to 0.498 to 4.985 µM of Hg(II) concentration, the nonlinear correlation was observed due to the saturation effect. LOD of Hg(II) ions over mesoporous $TiO_2$ NPs adsorption was $2.3 \times 10^{-9}$ molL$^{-1}$. Therefore, such evidence supported that the mesoporous $TiO_2$ NPs acting as efficient adsorbents, can be used to detect Hg(II) ions at ultra-trace levels from aqueous solution.

The Selectivity of a Designed Sensing System

The influences of foreign interferences on visualized detection Hg(II) ions $4.98 \times 10^{-7}$ molL$^{-1}$ are important key factors from the environmental point of view. Highly selective performance of designed sensing system in presence interfering cations such as Co(II), Ag(I), Ni(II), Pb(II), Ca(II), Zn(II), Mn(II), Cd(II), Fe(III)), and Cu(II), and anions such as $CH_3COO^-$, $CO_3^{-2}$, $NO_3^-$ and $SO_4^{-2}$ even at 1000 times greater than Hg(II) ions concentration (Table 1). The findings reveal that these diverse ions displayed insignificant color alteration and appreciable absorbance Hg(II)-DZ complex intensity. In addition, the selectivity of the Hg(II) ions during its detection was very high even in the presence of foreign ions at high concentrations, indicating a highly selective characteristic of mesoporous $TiO_2$ NPs.

TABLE 1

Summary of the color trend obtained for various interfering cations and anions to 1 ppm of Hg(II) ion solution at pH = 2.9 using 10 mg of mesoporous $TiO_2$.

| Foreign Cations and anions | 10 ppm | 100 ppm | 250 ppm |
|---|---|---|---|
| $Ag^+$ | No interference | No interference | No interference |
| $Al^{+3}$ | No interference | No interference | No interference |
| $Mn^{+2}$ | No interference | No interference | No interference |
| $Ni^{+2}$ | No interference | No interference | No interference |
| $Pb^{+2}$ | No interference | No interference | No interference |
| $Cu^{+2}$ | No interference | No interference | No interference |
| $Cd^{+2}$ | No interference | No interference | No interference |
| $Co^{+2}$ | No interference | No interference | No interference |
| $Mg^{+2}$ | No interference | No interference | No interference |
| $NO_3^-$ | No interference | No interference | No interference |
| $SO_4^{-2}$ | No interference | No interference | No interference |
| $Br^-$ | No interference | No interference | No interference |
| $Cl^-$ | No interference | No interference | No interference |
| $F^-$ | No interference | No interference | No interference |
| $CO_3^{-2}$ | No interference | No interference | No interference |
| $C_6H_5COO^-$ | No interference | No interference | No interference |
| $SO_4^{-2}$ | No interference | No interference | No interference |
| $CO_3^{-2}$ | No interference | No interference | No interference |
| SDS | No interference | No interference | No interference |

Figure 6A:
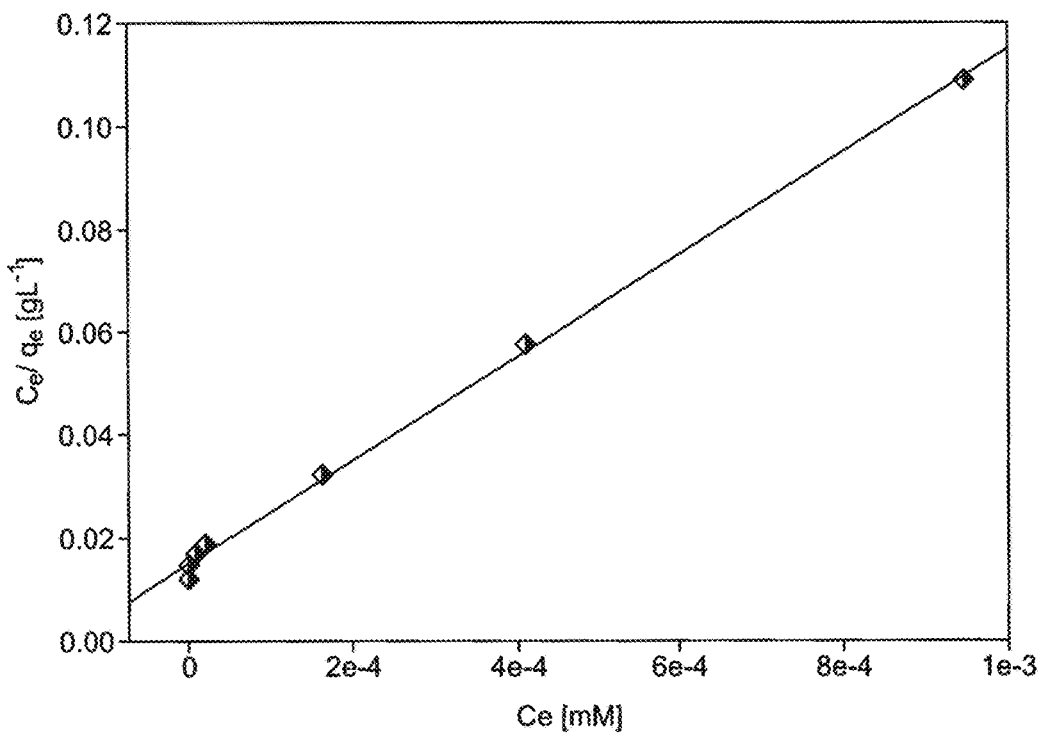
FIG. 6(a) shows adsorption behavior of Hg(II) ions of different concentration ranges ($4.98\times10^{-9}$ M-$4.985\times10^{-6}$ M) on mesoporous $TiO_2$ based sensor and equilibrium data applying the Langmuir isotherm model.

The adsorption capacity of the constructed visualized sensing system was estimated based on mesoporous $TiO_2$ NPs at diverse amounts utilizing the following equation. $Q_t = (C_o - C_t)V/m$, $Q_t$ is the adsorbed at saturation time t, m is the mass of adsorbent, $C_o$ and $C_t$ corresponded to concentration of Hg(II) ions at t=0 and at saturation time, respectively, V is the volume of solution. The amount of mesoporous $TiO_2$ NPs employed at 2.5, 5, 7.5, 10 and 12.5 mg corresponded to the adsorption capacity at 0.0031, 0.00173, 0.00125, 0.00103 and 0.0008 mmol/g, respectively. Adsorption behavior of Hg(II) ions on mesoporous $TiO_2$ based sensor has been evaluated and equilibrium data was investigated applying the model of Langmuir isotherm. This model provides the theoretical ultimate adsorption capacity and evaluation of the adsorption mechanism based on the formula: $C_e/q_e = C_e/Q_{max} + 1/Q_{max} K_L$, where $C_e$ represents the equilibrium Hg(II) ions concentration (mM), $q_e$ represents adsorbed Hg(II) ions amount at equilibrium concentration by mesoporous $TiO_2$ NPs based sensor (mmol/g), $Q_{max}$ represents extreme adsorption capacity (mmol/g) and $K_L$ is the Langmuir binding constant which describes the adsorption energy (L/mmol) as depicted in FIG. 6(a). $K_L$ and $Q_{max}$ were derived from the intercept and slope values obtained from the linear curve of $C_e/q_e$ versus $C_e$ to determine slope $1/Q_{max}$ and intercept $1/Q_{max} K_L$. Degree of the suitability of mesoporous $TiO_2$ based sensor towards the Hg(II) ions was described by constant of separation factor ($R_L$) which can be estimated by equation: $R_L = 1/1 + K_L C_o$, where $C_o$ is the initial Hg(II) ions concentration and $K_L$ is Langmuir equilibrium constant. This achieved value of dimensionless separation factor constant ($R_L$) obeys trend $0 < R_L < 1$ represents an appropriate adsorption approach while $R_L > 1$ represent unsuitably; and $R_L = 0$ means irreversible whereas $R_L = 1$ represent linear [A. M. Donia, A. A. Atia, K. Z. Elwakeel. J. Hazard. Mater. 2008; (151:372-379)].

Referring to FIG. 6(a) the model of Langmuir isotherm for diverse Hg(II) ions concentration ($4.98 \times 10^{-9}$ M-$4.985 \times 10^{-6}$ M) onto $TiO_2$ NPs at pH value ~2.9 is exhibited. The findings reveal that the adsorption values can be matched rationally with the Langmuir equation as depicted in FIG. 6(a) reflecting the validity of the Langmuir model. The slope $Q_{max}$ and intercept $K_L$ values were determined to be 0.01 mmol/g and 6579 L/mmol with the correlation coefficient (R2) about 0.997, represents the curve fitting well. According to the calculated $R_L$ value between 0.0296-0.968, indicating the condition 0<RL<1 which denotes that adsorption of Hg(II)-DZ complex over mesoporous $TiO_2$, NPs are favorable from aqueous solution. The adsorption capacity was estimated to be 0.00103 mmol/g employing 10 mg $TiO_2$ based sensing system and Hg(II) ions are $4.985 \times 10^{-7}$ M solution, which is consistent with $Q_{max}$ indicating that Hg(II) ions adsorption over mesoporous $TiO_2$ NPs as backbone adsorbent was effectively contributed in the presence of DZ probe.

Regeneration of the Sensing System

Figure 6B:
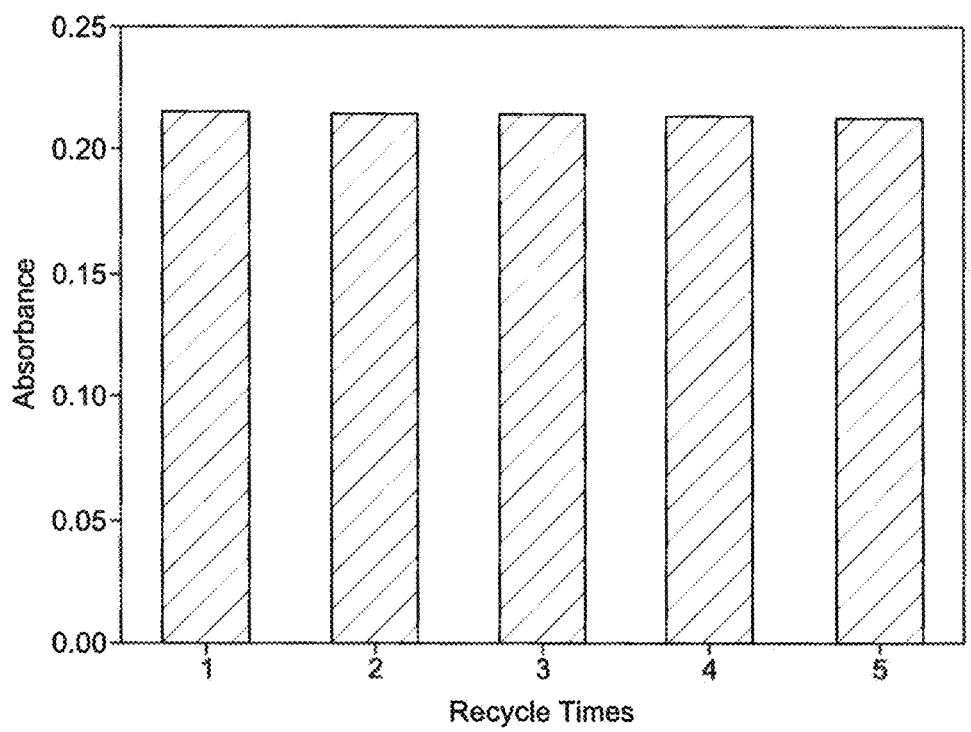
FIG. 6(b) shows stability of newly constructed visualized Hg-DZ complex over mesoporous $TiO_2$ NPs after five regeneration cycles through the self-cleaning of Hg(II)-DZ/$TiO_2$ sensor.

Stability of newly constructed visualized Hg-DZ complex over mesoporous $TiO_2$ NPs was evaluated through no elution of any colored moiety during the separation of Hg-DZ complex. The collected transparent filtrate confirmed that steadily integrated construction between Hg-DZ complex and mesoporous $TiO_2$ NPs which provides efficient removal and visual detection of Hg (II) ions. One of the key factors of the suggested sensing system is that it can regain almost the same adsorbing capacity, or it can be reused for the Hg (II) detection even after five cycles of analysis. The large $TiO_2$ bandgap provides an advantageous method to restore the sensor upon illumination same as a pristine one, according to the photodegradation of the adsorbed organic moiety. For the regeneration of the constructed Hg-DZ/$TiO_2$ sensor, firstly, it was exposed to UV illumination at $\lambda \sim 365$ nm for three hours, in order to degrade the DZ molecule and then it was leached by 0.001M $HNO_3$ to remove the Hg(II) ions. Finally, it was washed three times with $C_2H_5OH$ and $H_2O$, continued by drying at 110° C. for three hours to use again for visual inspection of Hg(II) ions. After five times of regeneration cycles, there was no significant change in visual detection and adsorption capacity of the constructed Hg(II)-DZ/$TiO_2$ sensor (FIG. 6b). The self-cleaning of [Hg-DZ]/$TiO_2$ sensor through photodegradation process was conducted by UV illumination to significantly improve the capability of the mesoporous $TiO_2$ NPs to recapture [Hg-DZ] complex easily. Both the extent of recovery and the recovery time was promoted by self-cleaning approach under UV illumination [T. M. Khedr, S. M. El-Sheikh, A. A. Ismail, D. W. Bahnemann *Optical Materials.* 2019; (88:117-1270]; [M. W. Kadi, A. A. Ismail, R. M. Mohamed, D. W. Bahnemann *Sep. Purif. Tech.* 2018; (205:66-73)]; [M. F. Atitar, A. A. Ismail, S. A. Al-Sayari, D. W. Bahneman, D. Afanasev, A. V. Emeline. *Chem. Eng. J.* 2015; (264:417-424)]; [A. A. Ismail and D. W. Bahnemann *J. Mater. Chem.* 2011; (21:11686-11707)]. Upon UV illumination of [Hg-DZ]/$TiO_2$, different species of oxidizing agents such as .OH and $O_2^-$. were created onto the $TiO_2$ NPs Immediately formed, these reactive oxidizing species then launch to the surface and degrade adsorbed DZ probe. In general, the mesoporous $TiO_2$ NPs were adequately stabilized such that the NPs could maintain activity for several hundreds of repeated cycles without leaching of the underlying mesoporous $TiO_2$ NPs [F. Liang, T. L. Kelly, L-b. Luo, H. Li, M. J. Sailor, Y. Y. Li. *ACS Appl. Mater. Interfaces.* 2012; (4: 4177-4183)].

The methods of the present disclosure show several advantages for the detection and measurement of the one or more heavy metals. One advantage of the embodiments according to the present disclosure is rapid and visible detection of one or more heavy metals. Another advantage of the method of the present disclosure in determining the concentration of the one or more heavy metals is determining an accurate amount of heavy metals at nanomolar concentration. Yet another advantage of the embodiments of the present disclosure is that the methods are fast, simple, robust, reproducible, sensitive, cost effective and specific enough to measure heavy metals, qualitatively and quantitatively.

It is understood that the examples, embodiments and teachings presented in this application are described merely for illustrative purposes. Any variations or modifications thereof are to be included within the scope of the present application as discussed.

What is claimed is:

1. A method of detecting one or more heavy metals in a sample solution, the method comprising:
    adding a dye to the sample solution containing the one or more heavy metals to form a metal-dye complex, wherein the one or more heavy metals are in the sample solution at a nanomolar concentration of about $2.0 \times 10^{-9}$ to $5.0 \times 10^{-9}$ $molL^{-1}$; then
    adding an adsorbent consisting of mesoporous $TiO_2$ nanoparticles (NPs) to the sample solution to preconcentrate the metal-dye complex onto a surface of the mesoporous $TiO_2$ NPs; and
    detecting a presence of the one or more heavy metals based on change in color within about 5-30 seconds via a naked eye.

2. The method of claim 1, wherein the dye is selected from a group comprising dithizone, coumarin, rhodamine derivatives, azo dyes, boron-dipyrromethene (BODIPY) dyes, 2-[3-(2-aminoethylsulfanyl) propylsulfanyl] ethanamine, fluorescein derivatives, cyanine dyes, or a combination thereof.

3. The method of claim 1, wherein the sample solution comprises the one or more heavy metals from a group comprising mercury, lead, cadmium, arsenic, nickel, chromium, cobalt, zinc, selenium, and salts thereof.

4. The method of claim 3, wherein the sample solution comprises mercury ions thereof.

5. The method of claim 1 further comprising, using the mesoporous $TiO_2$ NPs for at least 5 cycles of detection.

6. The method of claim 1 further comprising, detecting the one or more heavy metals in the sample solution at a nanomolecular concentration of about $2.3 \times 10^{-9}$ $molL^{-1}$.

7. The method of claim 1 further comprising, preconcentrating the one or more heavy metals in the sample solution before detection.

8. The method of claim 1, wherein the sample solution is selected from a group comprising drinking water, industrial effluents, bodily fluid, or a beverage suitable for human consumption.

* * * * *